(12) United States Patent
Sutton et al.

(10) Patent No.: US 7,618,786 B2
(45) Date of Patent: Nov. 17, 2009

(54) METHOD FOR IDENTIFYING MODULATORS OF HUMAN OREXIN-2 RECEPTOR

(75) Inventors: Steven W. Sutton, Carlsbad, CA (US); Timothy W. Lovenberg, San Diego, CA (US)

(73) Assignee: Janssen Pharmaceutica N.V., Beerse (BE)

( * ) Notice: Subject to any disclaimer, the term of this patent is extended or adjusted under 35 U.S.C. 154(b) by 528 days.

(21) Appl. No.: 10/537,732

(22) PCT Filed: Dec. 11, 2003

(86) PCT No.: PCT/US03/39491

§ 371 (c)(1),
(2), (4) Date: Jun. 7, 2005

(87) PCT Pub. No.: WO2004/054510

PCT Pub. Date: Jul. 1, 2004

(65) Prior Publication Data

US 2006/0035285 A1    Feb. 16, 2006

Related U.S. Application Data

(60) Provisional application No. 60/433,411, filed on Dec. 13, 2002.

(51) Int. Cl.
*G01N 33/53* (2006.01)
*G01N 33/566* (2006.01)
*G01N 33/567* (2006.01)
*C12N 15/85* (2006.01)
*C12N 5/08* (2006.01)

(52) U.S. Cl. .................... 435/7.1; 435/7.2; 435/7.21; 435/7.23; 435/325; 435/366; 435/371; 436/501

(58) Field of Classification Search .................. None
See application file for complete search history.

(56) References Cited

U.S. PATENT DOCUMENTS 5,589,351 A * 12/1996 Harootunian ............... 435/29

FOREIGN PATENT DOCUMENTS

WO    WO 01/85693    11/2001

OTHER PUBLICATIONS

Fults, et al, 1992, J. Neuropathol. Exper. Neurol., 51(3): 272-280.*

Huang, et al, 1997, Attenuation of Gi- and Gq-mediated signaling by expression of RGS4 or GAIP in mammalian cells. Proc. Natl. Acad. Sci., 94: 6159-6163.*

Chemelli, R.M. et al., "Narcolepsy in *orexin* Knockout Mice: Molecular Genetics of Sleep Regulation" *Cell*, 1999, 98, 437-451.

Chen, Chiung-Tong et al., "Pressor Effects of Orexins Injected Intracisternally and to Rostral Ventrolateral Medulla of Anesthetized Rats", *Am. J. Physiol.*, 2000, 278, R692-R697.

Cheng and Prusoff, "Relationship between the Inhibition Constant (k1) and the Concentration of Inhibitor which Causes 50 Per Cent Inhibition (i50) of an Enzymatic Reaction", *Biochemical Pharmacology*, 1973, 22, 3099-3108.

Conklin, B.R.et al., "Substitution of Three Amino Acids Switches Receptor Specificity of Gqα to that of Giα", *Nature*, 1993, 363, 274-276.

Fults, D.et al., "Establishment and Characterization of a Human Primitive Neuroectodermal Tumor Cell Line from the Cerebral Hemisphere", *Journal of Neuropathology and Experimental of Neuropathologists*, 1992, 51(3), 272-280.

Hara, J. et al., "Genetic Ablation of Orexin Neurons in Mice Results in Narcolepsy, Hypophagia, and Obesity", *Neuron*, 2001, 30, 345-354.

Kirchgessner, A.L. et al., "Orexin Synthesis and Response in the Gut" *Neuron*, 1999, 24, 941-951.

Lin, L. et al., "The Sleep Disorder Canine Narcolepsy is Caused by a Mutation in the Hypocretin (Orexin) Receptor 2 Gene", *Cell*, 1999, 98, 365-376.

Mignot, E. et al., "Complex HLA-DR and-DQ Interactions Confer Risk of Narcolepsy-Cataplexy in Three Ethnic Groups", *Am. J. Hum. Genet.*, 2001, 68, 686-699.

Milligan, G. et al., "Chimaeric Gα Proteins" Their Potential Use in Drug Discovery, *Trends Pharmacol*, 1999, 20, 118-124.

Mignot, E. et al., "Narcolepsy and the HLA System", *New England Journal of Medicine*, 2001, 344, 692.

Nakamura, T. et al., "Orexin-Induced Hyperlocomotion and Stereotypy are Mediated by the Dopaminergic System", *Brain Research*, 2000, 873 181-187.

Peyron, C. et al., "Neurons Containing Hypocretin (Orexin) project to Multiple Neuronal Systems", *The Journal of Neuroscience*, 1998, 18(23), 9996-10015.

Peyron, C. et al., "A Mutation in a Case of Early Onset Narcolepsy and a Generalized Absence of Hypocretin Peptides in Human Narcoleptic Brains" *Nature Medicine*, 2000, 6, 991-997.

(Continued)

*Primary Examiner*—Manjunath N Rao
*Assistant Examiner*—Sandra Wegert (57) ABSTRACT

The present invention provides a new method for identifying modulators of human orexin-2 receptor without utilizing recombinantly produced nucleic acid molecules encoding human orexin receptor protein. This method combines and utilizes known methods and cell lines selected for their natural expression of orexin-2 receptors to carry out the methods of the present invention. Exemplary methods of the present invention utilize PFSK-1 cells to produce non-recombinant human orexin-2 receptor protein.

8 Claims, 3 Drawing Sheets

OTHER PUBLICATIONS

Piper, D.C. et al., "The Novel Brain Neuropeptide, Orexin-A, Modulates the Sleep-Wake Cycle of Rats", *European Journal of Neuroscience*, 2000, 12, 726-730.

Samson, W.K. et al., "Cardiovascular Regulatory Actions of the Hypocretins in Brain" *Brain Research*, 1999, 831, 248-253.

Shirasaka, T. et al., "Sympathetic and Cardiovascular Actions or Orexins in Conscious Rats" *American J. Physiological Society*, 1999, 277, R1780-R1785.

Takahashi, N. et al., "Stimulation of Gastric Acid Secretion by Centrally Administered Orexin-A in Conscious Rats", *Biochemical and Biophysical Research Communications*, 1999, 254, 623-627.

van den Pol, A.N. "Hypothalamic Hypocretin (Orexin): Robust Innervation of the Spinal Cord", *The Journal of Neuroscience*, 1999, 19, 3171-3182.

Yamanaka, A. et al., "Orexins Activate Histaminergic Neurons via the Orexin 2 Receptor", *Biochemical and Biophysical Research Communications*, 2002, 290, 1237-1245.

Kane, J.K. et al., "Sensitivity of Orexin-A Binding to Phospholipase C Inhibitors, Neuropeptide Y and Secretin," *Biochemical and Biophysical Research Communications*, 2000, 272, 959-965.

Lee, J-H et al., "Solution structure of a new hypothalamic neuropeptide, human hypocretin-2/orexin-B," *Eur. J. Biochem.*, 1999, 266, 831-839.

Gartlon, J.E. et al., "Role of $OX_1$ and $OX_2$ receptors in the motor activity response to the orexins," *Society for Neuroscience Abstracts*, 2001, 27(1), 848.

Jaszberenyi, M. et al., "Effects of orexins on the hypothalamic-pituitary-adrenal system," *Journal of Neuroendocronology*, 2000, 12(12), 1174-1178.

Mignot, E. et al., "Sleeping with the hypothalamus: emerging therapeutic targets for sleep disorders," *Nature Neuroscience, Nature America, Inc.*, 2002, 5 Suppl., 1071-1075.

Sakurai, T. et al., "Oxerins and oxerin receptors: A family of hypothalamic neuropeptides and G Protein-coupled receptors that regulate feeding behavriour," *Cell*, 1998, 92, 573-585.

* cited by examiner

METHOD FOR IDENTIFYING MODULATORS OF HUMAN OREXIN-2 RECEPTOR

CROSS-REFERENCE TO RELATED APPLICATONS

This application is the National Stage of International Application No. PCT/US2003/039491 filed Dec. 11, 2003, which claims the benefit of U.S. Provisional Application No. 60/433,411, filed Dec. 13, 2002, the disclosures of which is incorporated herein by reference in its entirety.

FIELD OF THE INVENTION

This invention relates to assay systems for identifying modulators of cellular receptors. Specifically, the invention relates to assays for modulators of the orexin-2 receptor that utilize non-recombinant sources of the receptor.

BACKGROUND OF THE INVENTION

Orexin signaling is mediated by two receptors and two peptide agonists. The peptides (orexin A and orexin B) are cleavage products of the same gene, pre-pro orexin. In the central nervous system, neurons producing pre-pro orexin are found in the perifornical nucleus, the dorsal hypothalamus and the lateral hypothalamus (Peyron et al., 1998, J. Neurosci. 18: 9996-10015). Orexigenic cells in these regions project to many areas of the brain, extending rostrally to the olfactory bulbs and caudally to the spinal cord (Van den Pol, 1999, J. Neurosci. 19: 3171-3182). The orexins bind to two high affinty receptors, referred to as orexin-1 and orexin-2 receptors. The orexin-1 receptor is selective in favor of orexin A, while the orexin-2 receptor binds both orexins with similar affinities.

The broad CNS distribution of cells producing orexin, as well as cells expressing the orexin receptors, suggests involvement of orexin in a number of physiological functions, including feeding, drinking, arousal, stress, metabolism and reproduction. A recent report describing targeted necrosis of cells producing pre-pro orexin suggests that the most physiologically important roles of the orexins may be effects on arousal, feeding and metabolism (Hara et al., 2001, Neuron 30: 345-354).

Several lines of evidence indicate that the orexin system is an important modulator of arousal. Rodents administered orexin intracerebroventricularly spend more time awake (Piper et al., 2000, J. Neurosci. 12: 726-730. Orexin-mediated effects on arousal have been linked to orexin neuronal projections to histaminergic neurons in the tuberomammillary nucleus (TMN) (Yamanaka et al., 2002, Biochem. Biophys. Res. Comm. 290: 1237-1245). TMN neurons express the orexin-2 receptor primarily, and the orexin-1 receptor to a lesser extent. Rodents whose pre-pro orexin gene has been knocked out, or whose orexigenic neurons have been killed, display altered sleep/wake cycles similar to narcolepsy (Chemelli et al., 1999, Cell 98: 437-451; Hara et al., 2001, supra). Dog models of narcolepsy have been shown to have mutant or non-functional orexin-2 receptors (Lin et al., 1999, Cell 98: 365-376). Human narcolepsy appears to be linked to deficient orexin signaling, likely related to immune ablation of orexinergic neurons in the lateral hypothalamus (Mignot et al., 2001, Am. J. Hum. Genet. 68: 686-699; Minot & Thorsby, 2001, New England J. Med. 344: 692), or, in rare cases, to mutations in the orexin-2 gene (Peyron et al., 2000, Nature Med. 6: 991-997).

Disorders of the sleep-wake cycle are therefore likely targets for orexin-2 receptor modulator activity. Examples of sleep-wake disorders that may be treated by agonists or other modulators that up-regulate orexin-2 receptor-mediated processes include narcolepsy, jet lag (sleepiness) and sleep disorders secondary to neurological disorders such as depression. Examples of disorders that may be treated by antagonists or other modulators that down-regulate orexin-2 receptor-mediated processes include insomnia, restless leg syndrome, jet lag (wakefulness) and sleep disorders secondary to neurological disorders such as mania, schizophrenia, pain syndromes and the like.

The orexin system also interacts with brain dopamine systems. Intracerebroventricular injections of orexin in mice increase locomotor activity, grooming and stereotypy, these behavioral effects are reversed by administration of D2 dopamine receptor antagonists (Nakamura et al., 2000, Brain Res. 873: 181-187). Therefore, orexin-2 modulators may be useful to treat various neurological disorders; e.g., agonists or up-regulators to treat catatonia, antagonists or down-regulators to treat Parkinson's disease, Tourette's syndrome, anxiety, delerium and dementias.

Orexins and their receptors have been found in both the myenteric and submucosal plexus of the enteric nervous system, where orexins have been shown to increase motility in vitro (Kirchgessner & Liu, 1999, Neuron 24: 941-951) and to stimulate gastric acid secretion in vitro (Takahashi et al., 1999, Biochem. Biophys. Res. Comm. 254: 623-627). Orexin effects on the gut may be driven by a projection via the vagus nerve (van den Pol, 1999, supra), as vagotomy or atropine prevent the effect of an intracerebroventricular injection of orexin on gastric acid secretion (Takahashi et al., 1999, supra). Orexin receptor antagonists or other down-regulators of orexin receptor-mediated systems are therefore potential treatments for ulcers, irritable bowel syndrome, diarrhea and gastroesophageal reflux.

Body weight may also be affected by orexin-mediated regulation of appetite and metabolism. Some effects of orexin on metabolism and appetite may be mediated in the gut, where, as mentioned, orexins alter gastric motility and gastric acid secretion. Orexin antagonists therefore are likely to be useful in treatment of overweight or obesity and conditions related to overweight or obesity, such as insulin resistance/ type II diabetes, hyperlipidemia, gallstones, angina, hypertension, breathlessness, tachycardia, infertility, sleep apnea, back and joint pain, varicose veins and osteoarthritis. Conversely, orexin agonists are likely to be useful in treatment of underweight and related conditions such as hypotension, bradycardia, ammenorrhea and related infertility, and eating disorders such as anorexia and bulimia.

Intracerebroventricularly administered orexins have been shown to increase mean arterial pressure and a heart rate in freely moving (awake) animals (Samson et al., 1999, Brain Res. 831: 248-253; Shirasaka et al., 1999, Am. J. Physiol. 277: R1780-R1785) and in urethane-anesthetized animals (Chen et al., 2000, Am. J. Physiol. 278: R692-R697), with similar results. Orexin receptor agonists may therefore be candidates for treatment of hypotension, bradycardia and heart failure related thereto, while orexin receptor antagonists may be useful for treatment of hypertension, tachycardia and other arrhythmias, angina pectoris and acute heart failure.

From the foregoing discussion, it can be seen that the identification of orexin receptor modulators, particularly modulators of the orexin-2 receptor, will be of great advantage in the development of therapeutic agents for the treatment of a wide variety of disorders that are mediated through these receptor systems. There exists a need in the art for improved methods for identifying modulators of human orexin-2 receptor, particularly methods that do not require the use of recombinant DNA molecules encoding the human orexin-2 receptor. Such improved methods can facilitate the rapid processing of chemical libraries to identify modulators of the human orexin-2 receptor, and preferably will also be amenable to automation, thereby providing substantial commercial advantages for new drug discovery and development applications. The present invention is believed to satisfy these needs and to provide other related advantages.

Citation of a reference herein shall not be construed as an admission that such reference is prior art to the present invention. All publications referred to herein are incorporated by reference in their entireties.

SUMMARY OF THE INVENTION

The present invention relates to methods for identifying modulators of the human orexin-2 receptor, utilizing non-recombinant cell lines that express the orexin-2 receptor. A preferred cell line is known as the PFSK-1 cell line. In typical embodiments of the invention, whole cells as well as fractions or components thereof are utilized as a non-recombinant source of human orexin-2 receptor. Thus, non-recombinant cell lines provide sufficient quantities of orexin-2 receptors for performing assays to test compounds for their ability to modulate the receptor, without requiring the use of recombinantly produced nucleic acid molecules encoding the receptor.

According to one aspect of the invention, a method for identifying compounds that modulate human orexin-2 receptor activity is provided. The method comprises combining a putative modulator of human orexin-2 receptor activity with human orexin-2 receptors contained within membranes of cells non-recombinantly possessing the human orexin-2 receptor, and measuring an effect of the modulator on activity of the human orexin-2 receptor. In one embodiment, the human orexin-2 receptors are contained within membranes of intact cells. In another embodiment, the orexin-2 receptors are contained within membrane structures such as isolated membrane fragments, unilamellar vesicles and multilamellar vesicles. In a preferred embodiment, the cells possessing the human orexin-2 receptor are PFSK-1 cells. Several types of assays may be performed within this aspect of the invention. In one embodiment the effect measured is binding of the putative modulator to the orexin-2 receptors. In another embodiment, the effect measured is competition of the putative modulator with a known ligand of the human orexin-2 receptor for binding to the receptors. In another embodiment, the effect measured is modulation of a human orexin-2 receptor intracellular second messenger, such as cAMP, $Ca^{++}$, or a reporter gene product In a preferred embodiment, the intracellular second messenger is $Ca^{++}$ and is detected with a fluorescent $Ca^{++}$ indicator.

Another aspect of the invention features a kit for use in identifying compounds that modulate human orexin-2 receptor activity. The kit typically comprises human orexin-2 receptors contained within membranes of cells possessing the human orexin-2 receptor, and instructions for use of the receptors to identify compounds that modulate human orexin-2 receptor activity. Kits may comprise intact cells possessing human orexin-2 receptors. They may further comprise additional components such as known ligands of the orexin-2 receptor, reagents for detecting an effect of a putative modulator on orexin-2 receptor activity, and/or one or more buffers or diluents for practicing an assay to identify compounds that modulate human orexin-2 receptor activity.

According to another aspect of the invention, compounds identified using the above described methods are provided, wherein such compounds were not previously known to be a modulator of a human orexin-2 receptor. Such compounds may be agonists, antagonists, or inverse agonists of a human orexin-2 receptor or may modulate a $Ca^{++}$ channel activated by the human orexin-2 receptor.

Further aspects of the invention feature pharmaceutical compositions comprising a pharmaceutically acceptable carrier and compounds identified by the foregoing methods. Methods of using these pharmaceutical compositions to treat patients for conditions mediated by the orexin-2 receptor are also provided. In one embodiment, a condition mediated by a high amount or activity of a human orexin-2 receptor is treated by administration of a pharmaceutical composition of a type that lowers the amount or activity of the orexin-2 receptor. Such conditions include sleep/wake transition disorders, insomnia, hypermetabolism, hypertension, tachycardia, obesity, Parkinson's Disease, Tourette's Syndrome, anxiety, delirium and dementia. In another embodiment, a condition mediated by a low amount or activity of a human orexin-2 receptor is treated by administration of a pharmaceutical composition of a type that increases the amount or activity of the orexin-2 receptor. Such conditions include narcolepsy, jet lag, hypometabolism, hypotension, bradycardia and lack of appetite.

DETAILED DESCRIPTION OF THE INVENTION

The present invention provides methods for the identification of compounds that have the ability to modulate the activity of the human orexin-2 receptor. Methods such as those described herein are typically thought to require cells that express a recombinant receptor. However, the inventors have determined that these methods may be accomplished without the use of recombinantly produced nucleic acid molecules encoding the human orexin-2 receptor. Instead, non-recombinant cell lines that produce the orexin-2 receptor may be utilized. One such cell line is the known and commercially available PFSK-1 cell line (available from the American Type Culture Collection, ATCC Accession No. CRL-2060). Other such cell lines may be identified using defined methods, as described below. Modulators of the orexin-2 receptor that can be identified by the methods describe herein include agonists, antagonists, and inverse agonists. As used herein, the term "modulator" refers to an agent that increases or decreases the amount or activity of a receptor. Modulators may be any type of molecule, including but not limited to DNA, RNA, peptides, proteins, or non-proteinaceous organic or inorganic molecules. The term "agonist" refers to a compound that binds to a receptor, resulting in a biological effect associated with activity of the receptor. The term "antagonist" refers to a compound that blocks at least one biological effect associated with activity of a receptor (usually by binding to the receptor). The term inverse agonist refers to a compound that binds to a constitutively active receptor and reduces a biological effect associated with the constitutive activity of the receptor.

Modulators identified in the assays disclosed herein are useful, for example, as therapeutic agents, prophylactic agents, and diagnostic agents. Indications for the therapeutic agents include, but are not limited to, effects on arousal, feeding, metabolism, narcolepsy, hormone secretions, stress and reproductive system effects. Specifically, modulators that increase the amount or activity of orexin-2 receptors, as identified using the methods of the present invention, may be used to treat conditions such as narcolepsy, bradycardia, hypotension, hypometabolism and eating/appetite disorders leading to underweight conditions. Modulators that decrease the amount or activity of orexin-2 receptor are expected to be useful in the treatment of conditions such as insomnia, restless legs syndrome, pain, tachycardia, hypertension, angina pectoris, myocardial infarction, asthma, obesity, fertility (birth control), infertility, amenorrhea (dietary, emotional, pathologic, or due to stress), fluid imbalance, ulcers, diarrhea, constipation, irritable bowel syndrome, or various forms of dyskinesia.

One way to understand how human orexin-2 receptors are involved in these many physiological processes is to develop chemical modulators (agonists, antagonists, and inverse agonists) of the receptor as research tools and therapeutic entities. Non-recombinant host cells expressing the human orexin-2 receptor, such as the PFSK-1 cell line, are used to provide materials for a screening method to identify such agonists and antagonists. As such, this invention directly teaches a way to identify new agonists and antagonists of the human orexin-2 receptor that may prove useful as research tools or may be used as therapeutics to treat disorders directly or indirectly involving orexin-2 receptors.

The PFSK-1 cell line is exemplified herein for the assays of the present invention. The PFSK-1 cell line is a human primitive neuroectodermal tumor cell line from the cerebral hemisphere (Fults et al. (1992) J. Neuropath. Exp. Neurol. 51: 272-280). The cell line was identified as expressing the orexin-2 receptor through a DNA microarray screen of mRNA produced by a large number of cell lines. The PFSK-1 cell line was confirmed to produce sufficient amounts of the orexin-2 receptor to be suitable for use in the assays described herein. Though the PFSK-1 cell line was the only one identified as suitable in the inventors' initial DNA microarray screen, it is clear that additional rounds of such screening may be used to identify other suitable cell lines, in accordance with standard methodologies. Now that one cell line has been identified, other cell lines subsequently identified may be compared with PFSK-1 cells to determine if they produce sufficient orexin-2 receptor to be suitable for use in the present invention.

Assays to detect compound interaction or modulation of the human orexin-2 receptor include, but are not limited to, direct ligand binding assays, competitive (or displacement) ligand binding assays, or functional assays that measure the response of the receptor to the ligand, for example by measurement of changes in intracellular second messengers. Each of these assays may be performed using intact cells. Some of the assays, e.g., binding or competition assays, may be performed on orexin-2 receptor-containing membranes isolated from cells. As is known in the art, membrane fragments or vesicles comprising the receptor may be utilized for this type of assay.

A preferred assay system of the invention utilizes living PFSK-1 cells and the measurement of an intracellular second messenger as an indicator of the ability of candidate compounds to modulate the orexin-2 receptor. In one embodiment, a change in intracellular $Ca^{++}$, through the action of $G_q$ proteins, is measured; e.g., by fluorescence as described in detail below. In another embodiment, a second message is elicited in PFSK-1 cells by transfection of the cells with gene constructs conferring expression of chimaeric $G\alpha$ proteins (Conklin et al., 1993, Nature 363: 274-276; Milligan & Reese, 1999, Trends Pharmacol. Sci.20:118-124).

An exemplary assay system of the invention utilizes living PFSK-1 cells and the measurement of changes in intracellular $Ca^{++}$, as affected by candidate modulator compounds. Binding of orexin-2 receptors by agonists elevates the intracellular free calcium ion concentration through activation of a $G_q$ protein and opening of voltage-activated plasmalemmal calcium channels (van den Pol et al., 1998, supra). This effect is monitored using a fluorescent $Ca^{++}$ indicator such as Fluo-3 AM (TefLabs, Austin, Tex.) and an instrument like the Molecular Devices (Sunnyvale, Calif.) FLIPR (Fluorescent Imaging Plate Reader).

Briefly, PFSK-1 cells are grown and maintained as described in Example 1 below. The cells are removed from confluent tissue culture dishes with trypsin-EDTA and plated in multi-well plates (e.g., Packard Viewplates, Meriden, Conn.). Adherent cells are grown to confluency, then loaded with the fluorescent dye. The complete growth medium is removed from the plate and the fluorescence indicator solution is added to each well. The plate is maintained for a pre-determined time under appropriate cell culture conditions. Measurements of changes in intracellular calcium concentrations are performed using the FLIPR instrument. The timing of compound addition is determined by the type of assay (agonist screen, agonist efficacy/$EC_{50}$ determination, antagonist screen or antagonist $pK_B$ assay) and the rate kinetics of the test compound(s), as would be understood by one of skill in the art.

For a standard antagonist $pK_B$ assay using the FLIPR, the device is set to record 60 exposures one second apart, then 20 exposures six seconds apart. An appropriate volume and concentration of compound, control or agonist is added after the first ten exposures. Appropriate statistics (such as the sum, maximum signal, or maximum—minimum signal for each well) describing the magnitude of the responses are compiled by the FLIPR software or by similar means using raw data files created by the FLIPR software.

For screening purposes, compounds can be tested at a single dose to determine the percentage stimulation or percentage inhibition of intracellular $Ca^{++}$ signaling compared to a known orexin agonist stimulus. In an agonist screen, the positive and negative controls are added to a separate column of the plate from the test compounds. In an antagonist screen, the compounds typically are delivered to the test wells, incubated to allow binding, and then an orexin agonist stimulus is added to the test wells. The control for the antagonist screen includes positive and negative controls to indicate the fluorescent response to a full agonist, as well as a baseline.

Agonism is analyzed to determine both efficacy (compared to a control orexin agonist) and $EC_{50}$. For this type of assay, a single multi-well plate may contain both a dose response of the test compound and a dose response of a control orexin agonist Antagonism is analyzed by calculating $K_B$ and $pK_B$ values for compounds found to inhibit increases in intracellular $Ca^{++}$ concentrations in the cells. This is accomplished by determining the $EC_{50}$ of an orexin agonist and comparing the $IC_{50}$ values determined from dilutions of antagonist compound(s) on a single multi-well plate of PFSK-1 cells loaded with Fluo-3 AM or a similar dye. In this case, all of the wells, except those used to determine the agonist's $EC_{50}$, are given the same concentration of the orexin agonist.

The $K_B$ is then determined after Cheng and Prusoff (1973), Biochem. Pharmacol. 22: 3099-3108, using the formula below:

$$K_B=IC_{50}/(1+(\{agonist\}/EC_{50}))$$

Since binding of the orexin-2 receptor by an agonist leads to the opening of membrane calcium ion channels, other means known to those skilled in the art could be used to assay orexin receptor activity on PFSK-1 cells. Examples of such methods include use of voltage sensitive fluorescent dyes (such as used in Molecular Devices' FLIPR Membrane Potential Assay Kit), patch clamping techniques and the like. Similarly, these methods could be used to screen for modulators of the relevant $Ca^{++}$ channel.

The present invention is also directed to methods for screening test compounds suspected of being modulators of the orexin-2 receptor for compounds that modulate the expression of DNA or RNA encoding human orexin-2 receptor as well as the function of the receptor protein in vivo. Compounds that modulate these activities may be DNA, RNA, peptides, proteins, or non-proteinaceous organic or inorganic molecules. Compounds may modulate by increasing or attenuating the expression of DNA or RNA encoding the orexin-2 receptor, or the function of the receptor protein. Compounds that modulate the expression of DNA or RNA encoding orexin-2 receptor or the function of orexin-2 receptor protein may be detected by a variety of assays utilizing PFSK-1 cells and/or fractions or components thereof. The presence or amount of orexin-2 receptor-encoding mRNA from cells containing same may be measured according to standard methods, including but not limited to "Northern" blot analysis and quantitative PCR. The presence or amount of orexin-2 receptor protein is also measurable by standard methods, such as by "Western" blot, immunoprecipitation or similar methods. Assays to measure function are described above, wherein function is indicated by the ability of the receptor to transduce a signal, i.e., to produce an intracellular second messenger. The assay may be a simple "yes/no" assay to determine whether there is a change in expression or function. The assay may be made quantitative by comparing the expression or function of a test sample with the levels of expression or function in a standard sample. Modulators identified in this process are useful as therapeutic agents, research tools, and diagnostic agents.

Kits containing human orexin-2 receptor protein produced by or derived from PFSK-1 cells may be prepared. Such kits are used to characterize or identify compounds that have the ability or activity of modulating the activity of human orexin-2 receptor. Such characterization is useful for a variety of purposes including but not limited to drug discovery and drug development to identify new drugs that modulate the activity of human orexin-2 receptor.

Kits containing the orexin-2 receptor protein from PFSK-1 cells may be prepared since these preparations will be generally useful to analyze and/or characterize the activity of a wide variety of heterologous compounds. Such kits will be particularly beneficial, for example, to investigators in gene discovery for expressing novel compounds as modulators of orexin-2 receptor protein. Such a kit would comprise a compartmentalized carrier suitable to hold in close confinement at least one container. The carrier would further comprise reagents such as receptor protein (within membranes or within whole or living cells) or control compounds suitable for detecting the modulation of the orexin-2 receptor proteins. The carrier may also contain a means for detection such as labeled ligands, labeled antigen or enzyme substrates or the like. Such kits are also used to detect the presence the receptor protein or peptide fragments in a sample. Such characterization is useful for a variety of purposes including but not limited to forensic analyses, diagnostic applications, and epidemiological studies.

Pharmaceutically useful compositions comprising modulators of human orexin-2 receptor activity, may be formulated according to known methods such as by the admixture of a pharmaceutically acceptable carrier. Examples of such carriers and methods of formulation may be found in Remington's Pharmaceutical Sciences. To form a pharmaceutically acceptable composition suitable for effective administration, such compositions will contain an effective amount of the protein, DNA, RNA, or modulator as the active ingredient.

Therapeutic or diagnostic compositions identified using the methods of the present invention are administered to an individual in amounts sufficient to treat or diagnose disorders in which modulation of human orexin-2 receptor-related activity is indicated. The effective amount may vary according to a variety of factors such as the individual's condition, weight, sex and age. Other factors include the mode of administration. The pharmaceutical compositions may be provided to the individual by a variety of routes such as intravenous, intraperitoneal, intranasal, subcutaneous, topical, oral and intramuscular.

The term "chemical derivative" describes a molecule that contains additional chemical moieties that are not normally a part of the base molecule (i.e., an orexin-2 receptor modulator identified by the methods of the invention). Such moieties may improve the solubility, half-life, absorption, etc. of the base molecule. Alternatively the moieties may attenuate undesirable side effects of the base molecule or decrease the toxicity of the base molecule. Examples of such moieties are described in a variety of texts, such as Remington's Pharmaceutical Sciences.

Compounds identified according to the methods disclosed herein may be used alone at appropriate dosages defined by routine testing in order to obtain optimal stimulation or inhibition of the orexin-2 receptor or its activity while minimizing any potential toxicity. In addition, co-administration or sequential administration of other agents may be desirable.

The present invention also has the objective of providing suitable topical, oral, systemic and parenteral pharmaceutical formulations for use in the novel methods of treatment using compounds identified via the present invention. The compositions containing compounds or modulators identified according to this invention as the active ingredient for use in the modulation of orexin-2 receptor receptors can be administered in a wide variety of therapeutic dosage forms in conventional vehicles for administration. For example, the compounds or modulators can be administered in such oral dosage forms as tablets, capsules (each including timed release and sustained release formulations), pills, powders, granules, elixirs, tinctures, solutions, suspensions, syrups and emulsions, or by injection. Likewise, they may also be administered in intravenous (both bolus and infusion), intraperitoneal, subcutaneous, topical with or without occlusion, or intramuscular form, all using forms well known to those of ordinary skill in the pharmaceutical arts. An effective but non-toxic amount of the compound desired can be employed as an orexin-2 receptor modulating agent.

The daily dosage of compositions identified according to the methods disclosed herein may be varied over a wide range from 0.01 to 1,000 mg per patient, per day. For oral administration, the compositions are preferably provided in the form of scored or un-scored tablets containing 0.01, 0.05, 0.1, 0.5, 1.0, 2.5, 5.0, 10.0, 15.0, 25.0, and 50.0 milligrams of the active ingredient for the symptomatic adjustment of the dosage to the patient to be treated. An effective amount of the drug is ordinarily supplied at a dosage level of from about 0.0001 mg/kg to about 100 mg/kg of body weight per day. The range is more particularly from about 0.001 mg/kg to 10 mg/kg of body weight per day. The dosages of the orexin-2 receptor modulators are adjusted when combined to achieve desired effects. On the other hand, dosages of these various agents may be independently optimized and combined to achieve a synergistic result wherein the pathology is reduced more than it would be if either agent were used alone.

Advantageously, compounds or modulators identified according to the methods of the present invention may be administered in a single daily dose, or the total daily dosage may be administered in divided doses of two, three or four times daily. Furthermore, these compounds can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

For combination treatment with more than one active agent, where the active agents are in separate dosage formulations, the active agents can be administered concurrently, or they each can be administered at separately staggered times.

The dosage regimen utilizing the compounds or modulators identified according to the present invention is selected in accordance with a variety of factors including type, species, age, weight, sex and medical condition of the patient; the severity of the condition to be treated; the route of administration; the renal and hepatic function of the patient; and the particular compound thereof employed. A physician or veterinarian of ordinary skill can readily determine and prescribe the effective amount of the drug required to prevent, counter or arrest the progress of the condition. Optimal precision in achieving concentrations of drug within the range that yields efficacy without toxicity requires a regimen based on the kinetics of the drug's availability to target sites. This involves a consideration of the distribution, equilibrium, and elimination of a drug.

Compositions or modulators identified according to the methods disclosed herein can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include, without limitation, sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

For liquid forms the active drug component can be combined in suitably flavored suspending or dispersing agents such as the synthetic and natural gums, for example, tragacanth, acacia, methyl-cellulose and the like. Other dispersing agents which may be employed include glycerin and the like. For parenteral administration, sterile suspensions and solutions are desired. Isotonic preparations which generally contain suitable preservatives are employed when intravenous, intraperitoneal, intramuscular or subcutaneous administration is desired.

Topical preparations containing the active drug component can be admixed with a variety of carrier materials well known in the art, such as, e.g., alcohols, aloe vera gel, allantoin, glycerine, vitamin A and E oils, mineral oil, PPG2 myristyl propionate, and the like, to form, e.g., alcoholic solutions, topical cleansers, cleansing creams, skin gels, skin lotions, and shampoos in cream or gel formulations.

The compounds or modulators identified according to the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds identified according to the present invention may also be delivered by the use of monoclonal antibodies as individual carriers to which the compound molecules are bound or coupled. The compounds or modulators identified via the present invention may also be coupled with soluble polymers as targetable drug carriers. Such polymers can include polyvinyl-pyrrolidone, pyran copolymer, polyhydroxypropylnethacryl-amidephenol, polyhydroxy-ethylaspartamidephenol, or polyethyl-eneoxidepolylysine substituted with palmitoyl residues. Furthermore, the compounds or modulators identified according to methods of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydro-pyrans, polycyanoacrylates and cross-linked or amphipathic block copolymers of hydrogels.

For oral administration, the compounds or modulators may be administered in capsule, tablet, or bolus form or alternatively they can be mixed in the animals' feed. The capsules, tablets, and boluses are comprised of the active ingredient in combination with an appropriate carrier vehicle such as starch, talc, magnesium stearate, or di-calcium phosphate. These unit dosage forms are prepared by intimately mixing the active ingredient with suitable finely-powdered inert ingredients including diluents, fillers, disintegrating agents, and/or binders such that a uniform mixture is obtained. An inert ingredient is one that will not react with the compounds or modulators and which is non-toxic to the animal being treated. Suitable inert ingredients include starch, lactose, talc, magnesium stearate, vegetable gums and oils, and the like. These formulations may contain a widely variable amount of the active and inactive ingredients depending on numerous factors such as the size and type of the animal species to be treated and the type and severity of the infection. The active ingredient may also be administered as an additive to the feed by simply mixing the compound with the feedstuff or by applying the compound to the surface of the feed. Alternatively the active ingredient may be mixed with an inert carrier and the resulting composition may then either be mixed with the feed or fed directly to the animal. Suitable inert carriers include corn meal, citrus meal, fermentation residues, soya grits, dried grains and the like. The active ingredients are intimately mixed with these inert carriers by grinding, stirring, milling, or tumbling such that the final composition contains from 0.001 to 5% by weight of the active ingredient.

The compounds or modulators may alternatively be administered parenterally via injection of a formulation consisting of the active ingredient dissolved in an inert liquid carrier. Injection may be either intramuscular, intravenous, intraperitoneal, intra-ruminal, intratracheal, or subcutaneous. The injectable formulation consists of the active ingredient mixed with an appropriate inert liquid carrier. Acceptable liquid carriers include the vegetable oils such as peanut oil, cotton seed oil, sesame oil and the like as well as organic solvents such as solketal, glycerol formal and the like. As an alternative, aqueous parenteral formulations may also be used. The vegetable oils are the preferred liquid carriers. The formulations are prepared by dissolving or suspending the active ingredient in the liquid carrier such that the final formulation contains from 0.005 to 10% by weight of the active ingredient.

Topical application of the compounds or modulators is possible through the use of a liquid drench or a shampoo containing the instant compounds or modulators as an aqueous solution or suspension. These formulations generally contain a suspending agent such as bentonite and normally will also contain an antifoaming agent Formulations containing from 0.005 to 10% by weight of the active ingredient are acceptable. Preferred formulations are those containing from 0.01 to 5% by weight of the instant compounds or modulators.

The following experimental examples are provided to illustrate the present invention and not to be considered to limit the present invention thereto.

EXAMPLE 1

Growth and Maintenance of PFSK-1 Cells

PFSK-1 cells were obtained from the American Type Culture Collection (CRL-2060; Manassas, Va.) and cultured as described by Fults et al., (1992, supra). Cells were grown on 10 or 15 cm tissue culture dishes (Corning Inc., Corning, N.Y.) in RPMI medium 1640 containing 25 mM Hepes and L-glutamine (Gibco/InVitrogen, Carlsbad, Calif.) supplemented with 10% fetal bovine serum (HyClone, Logan, Utah), 50 u/ml penicillin G, and 50 u/ml streptomycin sulfate. Cells grown on 10 cm dishes were grown in 10 ml complete medium and cells grown on 15 cm dishes were grown in 30 ml complete medium. Cells were passed every three to five days at a 1:5 dilution by aspirating away the medium, adding 2 ml/dish Gibco/Invitrogen Trypsin-EDTA solution, aspirating away the solution, incubating at room temperature for five minutes, and dispersing the cells into fresh plates using fresh complete medium. Cells were then maintained in incubators set to maintain 37° C. and 5% $CO_2$.

EXAMPLE 2

Fluorescence Assay of Intracellular Calcium Ion in PFSK-1 Cells

PFSK-1 cells grown and maintained as described in Example 1 were removed from a confluent tissue culture dish with trypsin-EDTA as described above and plated in a 96-well Packard Viewplate (Meriden, Conn.) at 50,000 cells/well in 100 μl/well complete medium. The next day the cells, which adhered to the Viewplate and grew to confluency, were loaded with the fluorescent dye Fluo-3. To prepare the Fluo-3 solution 20 μl of 2.3 μM Fluo-3 AM was mixed with 20 μl 20% F-127 detergent (Molecular Probes, Eugene, Oreg.) and that mixture was mixed into 10 ml Gibco/Invitrogen D-MEM:F12. The complete growth medium was then removed from the Viewplate and 100 μl of the Fluo-3 AM solution was added to each well. Appropriately diluted orexin-2 receptor inhibitors A, B, C or D (test compound, diluted in Dulbecco's phosphate-buffered saline) was added immediately after the Fluo-3 as required and the plate was then incubated at room temperature for 60 minutes. Test compounds were added to the wells in an isotonic, pH neutral vehicle, such as Dulbecco's phosphate-buffered saline.

EXAMPLE 3

Analysis of Effects of Test Compounds on Intracellular Calcium Ion in PFSK-1 Cells Following the incubation step described in Example 2, changes in intracellular calcium concentrations were measured using the FLIPR instrument (Molecular Probes, Eugene, Oreg.). The FLIPR device was set to record 60 exposures at one second apart, then 20 exposures at six seconds apart The FLIPR pipettor was set to deliver 30 μl of concentrated orexin B or buffer control after the first ten exposures. Data were analyzed using the maximum signal minus the minimum signal for each well, in arbitrary fluorescence units. The fluorescence values were further analyzed using GraphPad's (San Diego, Calif.) Prism program to determine orexin B's $EC_{50}$ and orexin inhibitor A's $IC_{50}$ to a 100 nM orexin B stimulus.

Antagonism was analyzed by calculating $K_B$ and $pK_B$ values for compounds found to inhibit increases in intracellular $Ca^{++}$ concentrations in the cells. This was accomplished by determining the $EC_{50}$ of an orexin agonist and comparing the $IC_{50}$ values determined from dilutions of antagonist compound(s) on a single multi-well plate of PFSK-1 cells loaded with Fluo-3 AM.

Figure 1:
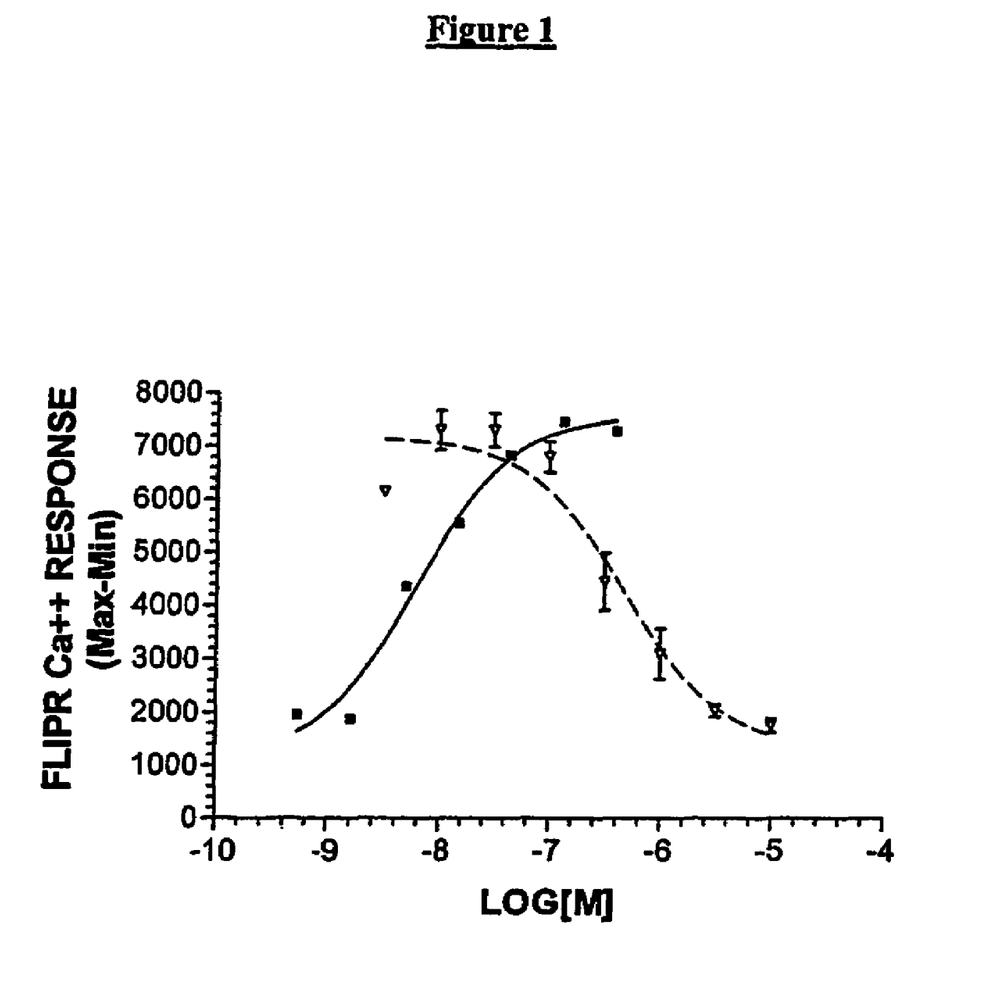
FIG. 1: Shows the dose dependent inhibition of 100 nM of the orexin-2 receptor ligand Orexin B, by orexin-2 receptor inhibitor A, as measured by intracellular $Ca^{++}$ in PFSK-1 cells. Filled squares=Orexin B alone; open triangles=Orexin B in the presence of inhibitor A.

The $K_B$ was then determined using the formula of Cheng and Prusoff. Results of three separate experiments, testing orexin 2 receptor inhibitors A, B, C and D are shown in FIG. 1 (inhibitor A), FIG. 2 (inhibitor B) and FIG. 3 (inhibitors C and D). Dose-dependent inhibition by each compound of 100 nM of Orexin B was measured; results are tabulated below.

Figure 2:
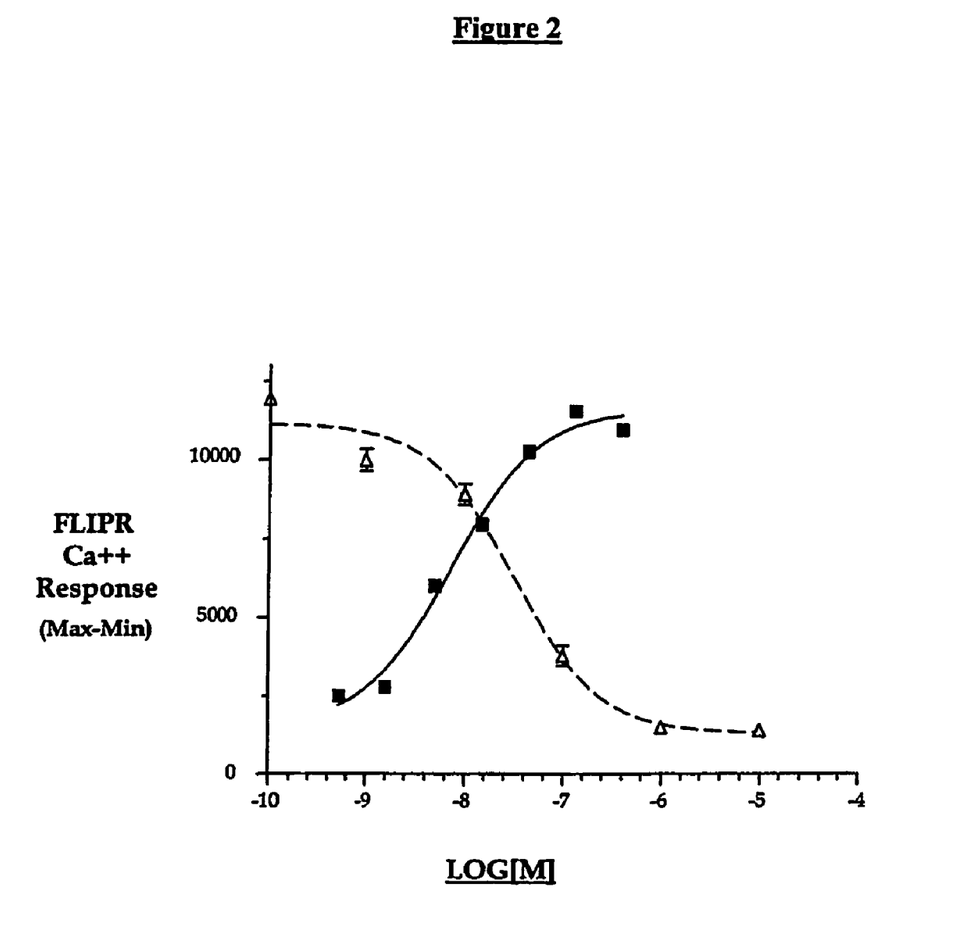
FIG. 2: Shows the dose dependent inhibition of 100 nM of the orexin-2 receptor ligand Orexin B, by orexin-2 receptor inhibitor B, as measured by intracellular $Ca^{++}$ in PFSK-1 cells. Filled squares=Orexin B alone; open triangles=Orexin B in the presence of inhibitor B.
Figure 3:
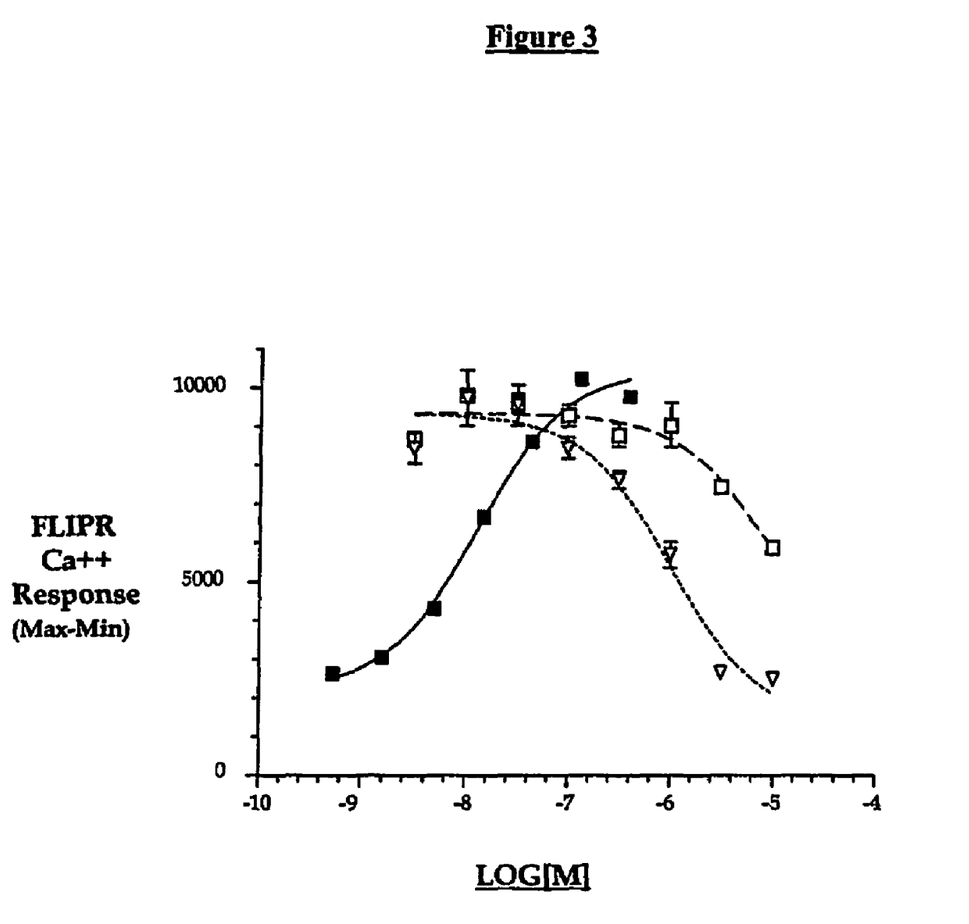
FIG. 3: Shows the dose dependent inhibition of 100 nM of the orexin-2 receptor ligand Orexin B, by orexin-2 receptor inhibitors C and D, as measured by intracellular $Ca^{++}$ in PFSK-1 cells. Filled squares=Orexin B alone; open triangles=Orexin B in the presence of inhibitor C; open squares=Orexin B in the presence of inhibitor D.

| Inhibitor | $IC_{50}$ (nM) | Orexin B $EC_{50}$ (nM) | Orexin B dose (nM) | $K_B$ (nM) | $pK_B$ |
|---|---|---|---|---|---|
| A | 477 | 6.2 | 100 | 28 | 7.6 |
| B | 32 | 7.4 | 100 | 2.2 | 8.7 |
| C | 1000 | 13 | 100 | 120 | 6.9 |
| D | >10,000 | 13 | 100 | >1200 | <5.9 |

Certain embodiments of the invention have been described and exemplified herein. The invention is not limited to the described and exemplified embodiments, but is capable of variation and modification within the scope of the appended claims.

We claim:

1. A method for identifying compounds that modulate human orexin-2 receptor activity, comprising:

a) combining a putative modulator of human orexin-2 receptor activity with human orexin-2 receptors contained within membranes of PFSK-1 cells non-recombinantly possessing the human orexin-2 receptor; and b) measuring the effect of the modulator on activity of the human orexin-2 receptor.

2. The method of claim 1, wherein the effect measured in step (b) is binding of the putative modulator to the orexin-2 receptors.

3. The method of claim 1, wherein the effect measured in step (b) is competition of the putative modulator with a known ligand of the human orexin-2 receptor for binding to the receptors.

4. The method of claim 1, wherein the effect measured in step (b) is modulation of a human orexin-2 receptor intracellular second messenger.

5. The method of claim 4, wherein the intracellular second messenger is selected from a group consisting of cAMP, $Ca^{++}$, and a reporter gene product.

6. The method of claim 5, wherein the cells are transfected with a Gα-protein DNA construct.

7. The method of claim 5, wherein the intracellular second messenger is $Ca^{++}$, detected with a fluorescent $Ca^{++}$ indicator.

8. The method of claim 1, adapted to distinguish the putative modulator as an agonist, antagonist or inverse agonist of the orexin-2 receptor.

* * * * *